US012491213B2

(12) United States Patent
Liu

(10) Patent No.: US 12,491,213 B2
(45) Date of Patent: Dec. 9, 2025

(54) TECHNICAL METHOD FOR TREATING VITILIGO THROUGH HAIR FOLLICLE MELANOCYTE STEM CELL TRANSPLANTATION

(71) Applicant: HAIKOU RENSHU DERMATOLOGY CLINIC CO., LTD, Haikou (CN)

(72) Inventor: Jingwei Liu, Haikou (CN)

(73) Assignee: HAIKOU RENSHU DERMATOLOGY CLINIC CO., LTD (CN)

( * ) Notice: Subject to any disclaimer, the term of this patent is extended or adjusted under 35 U.S.C. 154(b) by 792 days.

(21) Appl. No.: 17/758,405

(22) PCT Filed: Jan. 16, 2021

(86) PCT No.: PCT/CN2021/072340
§ 371 (c)(1),
(2) Date: Jul. 6, 2022

(87) PCT Pub. No.: WO2022/151450
PCT Pub. Date: Jul. 21, 2022

(65) Prior Publication Data
US 2023/0338430 A1 Oct. 26, 2023

(51) Int. Cl.
*A61K 35/36* (2015.01)
*C12N 5/071* (2010.01)

(52) U.S. Cl.
CPC ............ *A61K 35/36* (2013.01); *C12N 5/0626* (2013.01); *C12N 2506/091* (2013.01)

(58) Field of Classification Search
None
See application file for complete search history.

(56) References Cited

FOREIGN PATENT DOCUMENTS

CN 110339214 A * 10/2019 ............ A61K 35/36

* cited by examiner

*Primary Examiner* — Nghi V Nguyen

(57) ABSTRACT

The present disclosure discloses a technical method for treating vitiligo through hair follicle melanocyte stem cell transplantation. The technical method comprises the following steps: extraction of hair follicles; separation of hair follicles; in-vitro culture of hair follicle melanocyte stem cells; inactivation of hair follicles; and transplantation of hair follicle melanocyte stem cells. According to the present disclosure, outer root sheaths of hair follicles containing the hair follicle melanocyte stem cells are obtained through a precise extraction and separation method. Through in-vitro separation and culture and inactivation of hair follicles, a situation that vitiligo only turns black without hairs after surgery is achieved. Through precise transplantation, the original color of the punctate multi-hair follicle orifice can be restored, thereby achieving the purpose of rapidly removing white patches.

4 Claims, 1 Drawing Sheet

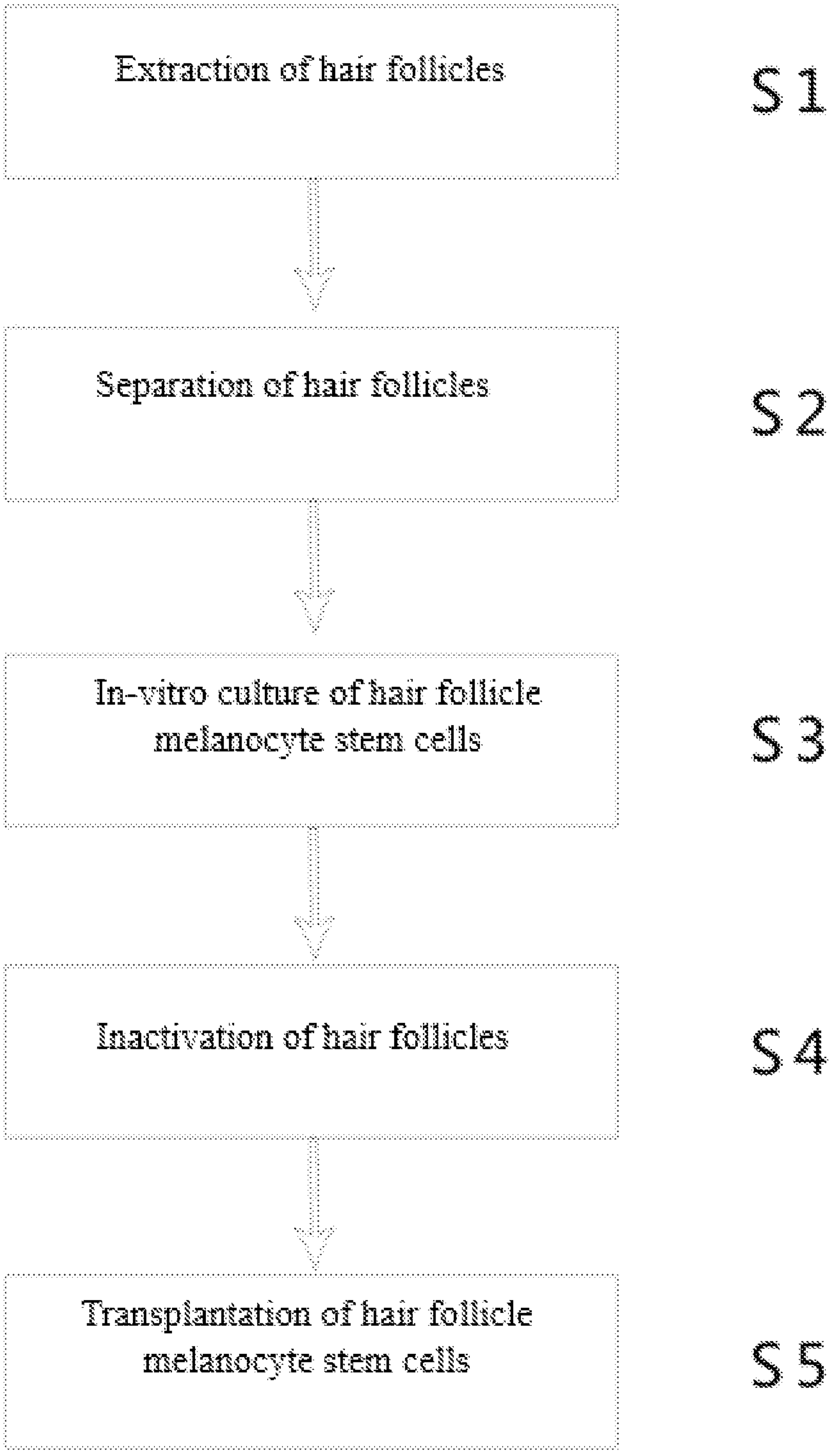
Extraction of hair follicles
S1
Separation of hair follicles
S2
In-vitro culture of hair follicle melanocyte stem cells
S3
Inactivation of hair follicles
S4
Transplantation of hair follicle melanocyte stem cells
S5

TECHNICAL METHOD FOR TREATING VITILIGO THROUGH HAIR FOLLICLE MELANOCYTE STEM CELL TRANSPLANTATION

TECHNICAL FIELD OF THE INVENTION

The present disclosure relates to the technical field of hair follicle transplantation, particularly to a technical method for treating vitiligo through hair follicle melanocyte stem cell transplantation.

BACKGROUND OF THE INVENTION

1. Epidemiological Investigation of Vitiligo

Vitiligo is a primary, limited or generalized skin mucosa depigmentation condition. In Chinese ancient medical books, vitiligo is called "epichrosis leucasmus". In general, the darker the skin, the higher the incidence rate, and the yellow people are between white and black people. In China, about 20 million of people have vitiligo with the morbidity being 0.1%-2.7%, and there are about 100 million of patients with vitiligo all over the world. Vitiligo is a common acquired, limited or generalized skin depigmentation, which is mainly caused by the disappeared melanocyte function of skins. Although this disease does not affect body health and physiological activity, great mental pressure and psychological burden are brought to patients since appearance is influenced, so as to give negative effects to life, study, work and other aspects of patients, thereby influencing the life quality of patients and even hindering the social communication and employment of patients. Thus, seeking a safe, effective and rapid vitiligo treatment method has important social and economic significance.

2. Technical Situations for Treatment of Vitiligo at Home and Abroad

In recent years, western medicine has gained progress in the aspects of pathogenesis, pathogenic mechanism and diagnosis of this disease, along with rapid development of basic subjects such as molecular biology; however, the pathogenic mechanism of vitiligo has not been completely clear so far. Vitiligo is an acquired hypopigmentation skin disease characterized by the reduction of local epidermal melanocytes and the formation of white spots. Its pathogenic mechanism has not been illustrated, and inheritance and immune factors play important role in this disease. At present, an evidence that vitiligo is an autoimmune disease: susceptibility genes and candidate genes such as SLEV1, AIS1 and HLA closely related to immune function or autoimmune diseases have been found; humoral and cellular immune mechanisms are both involved in the pathogenesis of vitiligo; patients with vitiligo often also have other autoimmune diseases at the same time; clinical treatment of vitiligo with immunomodulatory therapy has achieved good curative effects, but in such a way, vilitogo is easy to relapse. In terms of treatment, photochemotherapy, corticosteroid application, autologous epidermal transplantation, dermabrasion, 308NM excimer laser and other new treatments continuously emerge, but most of them have inaccurate curative effects or large side effects and high costs. Although there had been clinical reports about single-hair follicle transplantation being used for treatment of vitiligo 22 years ago: 21 cases of patients with vitiligo were treated with single-hair follicle transplantation by Na et al (in fact, tiny fragments of the outer root sheath were transplanted). However, treatment with single-hair follicle transplantation has the disadvantages of slow treatment speed and limited donor hair follicle source, which cannot meet the needs of transplantation treatment of vitiligo in a large area. Recently, there are reports about treatment of patients with vitiligo in a sable stage by culturing epidermal melanocyte suspension, but this treatment method cannot be accepted by patients because the suspension of folds and facial features cannot be fixed to lead to uncertain curative effect or too large side effects in the test stage; at present, there are reports about treatment of vitiligo with artificial tissue engineering, this method is suitable for treatment of patients with vitiligo in a large area, but the surgery requires dermabrasion, the postoperative re-coloration is uneven and vitiligo is easy to recur, so few people use it. Regardless of a suspension method or a tissue engineering method, it is needed to grind the epidermis in the transplantation area, which causes the patient to be painful so as to aggravate the risk of postoperative epidermal necrosis, so they cannot be widely used in clinical practice. Studies have shown that the inefficiency rate of vitiligo patients on various therapies can be up to more than 50%. In recent years, studies have found that the outer hair root sheath contains amelanotic melanocytes (AMMC), melanocyte stem cells and premelanocytes are collectively referred to as AMMC, and the premelanocytes are transition state from melanocyte stem cells to melanocytes. Hair follicle melanocytes stem cells (McSCs) are located in the bulge area at the lower end of the constant part of the hair follicle (upper ⅓ of the hair follicle), and most of them are under a quiescent condition, have chronic periodicity and an ability of maintaining self-updating, and are representative of typical regenerative stem cells. In 2002, Nishimura et al. did study through proliferation of melanocytes and found that stem cell factors expressed in the epidermis established a channel between the outer hair root sheath and the epidermis, and the melanocytes migrated from the hair follicles to the epidermis along this channel. Therefore, how to free the hair follicle melanocyte stem cells in the outer hair root sheath from the outer hair root sheath is a core of the present disclosure. based on the patented technology "Technical method of hair follicle melanocyte stem cell transplantation for the treatment of vitiligo (China Invention Patent No.: ZL201910769979.1, Certificate No. 4201136)" of our Haikou Renshu Dermatology Clinic Co., Ltd. and without dermabrasion, the colors of the white patches are restored, even the colors of the hair follicles are restored, and finally vitiligo is cured. The present application has made appropriate corrections and beneficial supplements and improvements to the granted Chinese patents.

The outer hair root sheath containing melanocyte stem cells prepared in the present disclosure is positioned and then transplanted to a specific layer suitable for the growth of melanocyte stem cells, which completely solves the source problem of vitiligo melanocytes. By extracting a small amount of hair follicles, this technique can truly achieve the purpose of treating large-area vitiligo. The surgery does not need to remove the epidermis of vitiligo, which greatly alleviates the pain of patients with vitiligo; the cure rate of once surgery can be up to more than 90%, thus it is a vitiligo therapy with the highest cure rate at present; it subverts the traditional vitiligo treatment method, which marks that vitiligo treatment has entered the era of stem cell transplantation.

SUMMARY OF THE INVENTION

The objective of the present disclosure is to provide an outer hair root sheath containing hair follicle melanocyte stem cells to treat vitiligo through minimally invasive surgery. The complete outer hair root sheath containing melanocyte stem cells is extracted and separated by using a vitiligo hair follicle extractor (Chinese patent certificate No. 11005086) invented by the company and cultured, so as to promote the differentiation and proliferation of the hair follicle melanocyte stem cells, activate and improve the activity of the hair follicle melanocyte stem cells through cultivation, and promote the rapid transformation of the melanocyte stem cells into the mature melanocytes; then the functionalized hair follicle melanocyte stem cells and the outer hair root sheath are accurately transplanted into the specific layer of vitiligo epidermis, thereby thoroughly solving the problem of melanocyte loss in the white patch area to solve the problems in the above background technology.

In order to achieve the above objective, the present disclosure provides the following technical solution:

Provided are a method and steps for treating vitiligo through hair follicle melanocyte stem cell transplantation:

Provided is a technical method for treating vitiligo through hair follicle melanocyte stem cell transplantation, wherein the technical method comprises the following steps:

step S1: extraction of hair follicles, specifically, extracting one unit of hair follicles by using a vitiligo hair follicle extractor (Chinese patent certificate No.: 11005086) invented by this company, wherein colored single hair follicles are firstly selected, hair follicles with white hairs are not selected, and meanwhile 5-60 ml of blood are drawn from patients and then centrifugally centrifuged to obtain required serum for later use;

step S2, separation of hair follicles, specifically, separating a single complete outer hair root sheath with epidermis and containing hair follicle melanocyte stem cells from the hair follicles under a 2-15× magnifying glass or electron microscope, wherein the outer hair root sheath contains all the melanocyte stem cells and mature melanocytes of hair follicles;

step S3, in-vitro culture of hair follicle melanocyte stem cells, specifically, putting the single-hair follicle of the complete outer hair root sheath containing the hair follicle melanocyte stem cells into a hair follicle storage ice box (Chinese patent certificate No.: 10098918) invented by the company for culture so as to enhance the activity of the hair follicle melanocyte stem cells, promoting the differentiation and proliferation of the hair follicle melanocyte stem cells and transformation into the mature melanocytes;

step S4, inactivation of hair follicles, specifically, inactivating hair follicles prior to transplantation by means of a dermoscope and a novel vitiligo hair follicle inactivation needle (Chinese patent certificate No.: 10979242); and step S5, transplantation of hair follicle melanocyte stem cells, specifically, implanting the outer hair follicle sheath containing the hair follicle melanocyte stem cells at the specific level of vitiligo by using an implant needle for treating vitiligo (Chinese patent certificate No.: 11440332) after inactivation of hair follicles so as to promote differentiation and proliferation of the melanocyte cells and formation of tissues and realize that the color of the punctate multi-hair follicle orifice can be restored, thereby achieving the purpose of rapidly removing white patches.

Further, the specific method of step S1 is as follows: one unit of hair follicles is extracted by using the vitiligo hair follicle extractor invented by this company, wherein colored single-hair follicles or double-hair follicles are firstly selected so as to facilitate separation, hair follicles with white hairs are not selected; and meanwhile 5-60 ml of blood are drawn from patients and then centrifugally separated to obtain required serum for later use.

Further, in the step S2, after the hair follicle is extracted by using a patent vitiligo hair follicle extractor, the hair follicle is separated under the 2-15× magnifying glass or electron microscope with an accuracy being up to 100%, so as to avoid that the hair follicle melanocyte stem cell and outer root sheath are damaged.

Further, in the step S3, in-vitro culture is performed on hair follicle melanocyte stem cells, specifically, the single hair follicle of the complete outer hair root sheath containing the hair follicle melanocyte stem cells is put into a hair follicle storage ice box (Chinese patent certificate No.: 10098918) invented by this company for culture so as to enhance the activity of the hair follicle melanocyte stem cells and promote the differentiation and proliferation of the hair follicle melanocyte stem cells and transformation into the mature melanocytes; the mature melanocytes are put into a special culture solution for culture at 0-4° C. for 60 min, and the cultured melanocyte cells are irradiated for 5-50 s with 308NM excimer laser for later use.

Further, the main components of the special culture solution are psoralea corylifolia injection, dexamethasone sodium phosphate injection, autologous serum, low-molecular-weight heparin sodium and normal saline.

Further, in the step S4, hair follicles cultured in the special culture solution are inactivated, specifically, first, hair follicle tails are held with hair follicle extraction forceps, the hair follicles are inactivated with a novel vitiligo hair follicle inactivation needle (Chinese patent certificate No.: 10979242) under the microscope, and the hair nipple is stabbed until hear the "snap" sound is heard and the liquid runs up, so as to inactivate the hair follicles and realize that vitiligo only turns black without hairs after surgery.

Further, in the step S5, the outer hair follicle sheath containing the hair follicle melanocyte stem cells is implanted based on hair follicles, specifically, under the positioning of the implantation positioning needle (Chinese patent certificate No.: 11438879), the above outer hair follicle sheath is implanted at the specific level of vitiligo by using an implant needle for treating vitiligo (Chinese patent certificate No.: 11440332), so as to thoroughly solve the source problem of vitiligo melanocyte cells, thereby achieving the purpose of curing vitiligo.

Compared with the prior art, the present disclosure has the beneficial effects:

1. The hair follicle outer hair root sheath containing hair follicle melanocyte stem cells is obtained through a unique external hair root sheath separation technology, and vitiligo is treated through transplantation surgery.
2. The present disclosure invents an in vitro culture technology of hair follicle melanocyte stem cells, by which the obtained hair follicle melanocyte stem cells are cultured in vitro through a special culture solution to convert more non-functional melanocyte stem cells into functional melanocyte stem cells, thereby promoting the rapid transformation of the hair follicle melanocyte stem cells into the mature melanocytes.
3. Through the hair follicle inactivation technology, the hair follicles prior to transplantation can be inactivated with the help of a magnifying glass or microscope and a hair follicle inactivation needle, so as to inactivate the hair follicles and realize that vitiligo only turns black without hairs after surgery.
4. The extracted hair follicle melanocyte stem cells are not affected by the body's endocrine and hormones. After culture and activation, they are accurately planted in the lesion area of white patches and are not affected by the disease area, so as to ensure the postoperative curative effect, promote the proliferation and differentiation of melanocytes and the formation of tissues, and realize the multicolor of punctate multiple hair follicles, so as to achieve the purpose of rapidly removing white patches.

BRIEF DESCRIPTION OF THE DRAWINGS

Accompanying drawings are intended to further understand the present disclosure and constitute one part of the specification, and used for explaining the present disclosure together with specific embodiments of the present disclosure, but not limited thereto; in which:

FIG. 1 is a flowchart of a technical method for treating vitiligo through hair follicle melanocyte stem cell transplantation according to the present disclosure.

DETAILED DESCRIPTION OF THE INVENTION

Next, preferred embodiments of the present disclosure will be described in detail in combination with drawings. It should be understood that the preferred embodiments described herein are only for illustrating and explaining the present disclosure but not limiting thereto.

The technical key points of the present disclosure are as follows: 1, in-vitro culture is performed on the obtained hair follicle melanocyte stem cells by using the in-vitro culture technology of the hair follicle melanocyte stem cells, specifically, main components psoralea corylifolia injection, dexamethasone sodium phosphate injection, autologous serum and normal saline are cultured for 60 min at 0-4° C., and then irradiated for 5-50 s by using 308NM excimer laser for later use; 2, the hair follicles prior to transplantation are inactivated by using the hair follicle inactivation technology with the help of the dermoscope and the hair follicle inactivation needle, and the method is as follows: first, hair follicle tails are held with hair follicle extraction forceps, the hair nipple was stabbed until hear the "snap" sound is heard and the liquid runs up, so that the hair follicles are inactivated and vitiligo only turns black without hairs after surgery.

Example 1

As shown in FIG. 1, the present disclosure provides a technical solution: a technical method for treating vitiligo through hair follicle melanocyte stem cell transplantation comprises the following steps:

step S1: extraction of hair follicles, specifically, one unit of hair follicles were extracted by using a vitiligo hair follicle extractor (Chinese patent certificate No.: 11005086) invented by this company, wherein colored single hair follicles were firstly selected, hair follicles with white hairs were not selected, and meanwhile 5-60 ml of blood from patients were drawn and then centrifugally separated to obtain required serum for later use;

step S2, separation of hair follicles, specifically, a single complete outer hair root sheath containing hair follicle melanocyte stem cells were separated from the hair follicle unit under the 2-15× magnifying glass or electron microscope;

step S3, in-vitro culture of hair follicle melanocyte stem cells, specifically, the extracted and separated single hair follicle were cultured in a special culture solution for later use, so as to enhance the activity of the hair follicle melanocyte stem cells and transformation into the mature melanocytes through culture;

step S4, inactivation of hair follicles, specifically, hair follicles prior to transplantation were inactivated by means of a dermoscope and a hair follicle inactivation needle; and step S5, transplantation of hair follicle melanocyte stem cells, specifically, the outer hair follicle sheath containing the hair follicle melanocyte stem cells was accurately implanted at the specific level of vitiligo by using a specially made implant needle after inactivation of hair follicles, so as to promote differentiation and proliferation of the melanocyte cells and formation of tissues and realize that the color of the punctate multi-hair follicle orifice can be restored, thereby achieving the purpose of rapidly removing white patches.

In this example, the specific method of step S1 was as follows: one unit of hair follicles was extracted by using a vitiligo hair follicle extractor invented by this company, wherein colored single-hair follicles or double-hair follicles were firstly selected, and hair follicles with white hairs were not selected; and meanwhile 5-60 ml of blood were drawn from patients and then centrifugally separated to obtain required serum for later use.

In this example, in the step S2, the complete outer hair root sheath of the melanocyte stem cell containing epidermis was separated from the hair follicle unit.

In this example, in the step S3, in-vitro culture was performed on the hair follicle melanocyte stem cells, specifically, the single hair follicles were put into a special culture solution for culture at 0-4° C. for 60 min, and then were irradiated for 5-50 s with 308NM excimer laser for later use, wherein the main components of the special culture solution were psoralea corylifolia injection, dexamethasone sodium phosphate injection, autologous serum and normal saline, the irradiated hair follicles were cultured in the special culture solution for later use, so that the enhancement of the activity of the melanocyte stem cells and transformation into the mature melanocyte stem cells were achieved through culture.

In this example, in the step S4, hair follicles cultured in the special culture solution were inactivated, specifically, hair follicle tails were first held with hair follicle extraction forceps, the hair follicles were inactivated with a novel vitiligo hair follicle inactivation needle (Chinese patent certificate No.: 10979242) under the microscope, and the hair nipple was stabbed until hear the "snap" sound was heard and the liquid runs up, so as to inactivate the hair follicles and realize that vitiligo only turned lack without hairs after surgery.

In this example, in the step S5, the outer hair follicle sheath containing the hair follicle melanocyte stem cells was accurately implanted at the special level of vitiligo by using a implantation needed for treating vitiligo (Chinese patent certificate No.: 11440332), so as to promote the proliferation and differentiation of melanocyte stem cells and formation of tissues and realize that the color of the punctate multi-hair follicle orifice was restored, thereby achieving the purpose of rapidly removing white patches.

Example 2

As shown in FIG. 1, the present disclosure provides a technical method for treating vitiligo through hair follicle melanocyte stem cell transplantation. Through the technical method in example 1, the hair follicle melanocyte stem cells were transplanted at the special level of vitiligo so as to promote the proliferation and differentiation of melanocyte stem cells and formation of tissues and realize that the color of the punctate multi-hair follicle orifice was restored, thereby achieving the purpose of rapidly removing white patches.

In this example, through the transplantation technology of the hair follicle melanocyte stem cells, the curing rate of vitiligo reached 90% or more.

The technical difficulties and surgical procedures of the present disclosure:

Technical difficulties: "survival rate" refers to a fact that whether transplanted melanocyte stem cells can be directly survived, which is related to subsequent treatment effects. Autologous melanocyte stem cells obtained by extraction have the characteristics that they are not affected by internal secretion and hormone of an organism, and cannot be affected by inpatient areas after being cultured and activated to be implanted in focal areas of vitiligo to ensure a postoperative curative effect.

surgical procedures: 1, one unit of hair follicle is extracted by using the vitiligo hair follicle extractor (Chinese patent certificate No.: 11005086), wherein hair follicle of the hair follicle melanocyte stem cell containing epidermis is extracted; the complete hair follicle outer root sheath of the hair follicle melanocyte stem cell containing epidermis is obtained through a special separation method; the hair follicles after extraction and separation are cultured into the special culture solution for 60 min at 0-4° C. and then irradiated for 5-50 s with 308NM excimer laser for later use, subsequently, the extracted hair follicles are inactivated with the help of a magnifying glass or microscope and a hair follicle inactivation needle to achieve a fact that vitiligo only turned black without hair after surgery; 2, "implantation" is a key point associated with survival of melanocyte stem cells, if the planting is too shallow, the survival rate is low, and the effect is not good, while if the implantation is too deep, the melanocyte stem cells cannot move to the hair follicle mouth of the epidermis of vitiligo along the outer hair root sheath to cause a reduced curative effect, and therefore the punctate multi-hair follicle orifice is re-colored as long as the melanocyte stem cells are accurately implanted at the special level of vitiligo.

The principle of the present disclosure: with the help of a WOOD lamp and an accurate dermoscopy imaging data report, the melanin loss degree and cell activity of patients are analyzed. The hair follicle melanocyte stem cells are extracted with a patented technology, the hair follicles are inactivated using the inactivation needle under the microscope through special culture and separation, and then the inactivated hair follicles are accurately implanted at the special level of vitiligo by using the specially made implantation needle so as to promote the proliferation and differentiation of melanocytes and formation of tissues and realize that the color of the multi-hair follicle orifice is restored, thereby achieving the purpose of rapidly removing white patches. This technology can rebuild the patient's autoimmune system in the vitiligo area and solves the problem of melanocyte inactivation, so that the treatment of vitiligo enters the era of minimally invasive surgery.

The above descriptions are only preferred embodiments of the present disclosure but not limit the present disclosure. Although the present disclosure has been illustrated in detail with reference to the above-mentioned examples, those skilled in the art still can make modification on the technical solution described in each example, or equivalent substitutions to parts of technical features. Any modifications, equivalent substitutions and improvements made within the spirit and principle of the present disclosure should be included within the protective scope of the present disclosure.

What is claimed is:

1. An in-vitro preparation method of hair follicle melanocyte stem cells comprising the following steps:

step S1: extracting one unit of hair follicles by using a vitiligo hair follicle extractor, wherein colored single-hair follicles or double-hair follicles are firstly selected, and the hair follicles with white hairs are not selected and meanwhile, 5-60 ml of blood are drawn from patients and then centrifugally separated to obtain required serum for in-vitro culture;

step S2, separating a single complete outer hair root sheath with epidermis and containing hair follicle melanocyte stem cells from the hair follicles under a 2-15× magnifying glass or electron microscope, wherein the outer single complete hair root sheath contains all the melanocyte stem cells and mature melanocytes extracted from the hair follicles;

step S3, putting the single-hair follicle of the complete outer hair root sheath containing the hair follicle melanocyte stem cells into a hair follicle storage ice box for culture, to enhance the activity of the hair follicle melanocyte stem cells and promote the differentiation and proliferation of the hair follicle melanocyte stem cells and transformation into the mature melanocytes, and culturing the mature melanocytes into a special culture solution at 0-4° C. for 60 min, and irradiating the cultured melanocytes for 5-50 s with 308NM excimer laser for later use wherein, the main ingredients of the special culture solution are psoralea corylifolia injection, dexamethasone sodium phosphate injection, autologous serum, low-molecular-weight heparin sodium and normal saline; and step S4, inactivating the hair follicles with the help of a dermoscope and a novel vitiligo hair follicle inactivation needle.

2. The in-vitro preparation method of the hair follicle melanocyte stem cells according to claim 1, wherein in the step S1 extraction of the hair follicles comprises extracting one unit of the hair follicles by using a vitiligo hair follicle extractor, wherein colored single-hair follicles or double-hair follicles are firstly selected to facilitate separation, the hair follicles with the white hairs are not selected, and meanwhile 5-60 ml of blood are drawn from patients and then centrifugally separated to obtain required serum for in-vitro culture of the hair follicle melanocyte stem cells.

3. The in-vitro preparation method of the hair follicle melanocyte stem cells according to claim 2, wherein in the step S2 the separation of the hair follicles, specifically; comprises separating a single complete outer hair root sheath with epidermis and containing the hair follicle melanocyte stem cells from the hair follicles under a 2-15× magnifying glass or electron microscope to extend the movement pathway of the hair follicle melanocyte stem cells and increase number of the mature melanocytes to enter the peripheries of more hair follicle orifices.

4. The in-vitro preparation method of the hair follicle melanocyte stem cells according to claim 1, wherein the step S4 in the in-vitro preparation method of hair follicle melanocyte stem cells comprises:

inactivating the hair follicles cultured with the special culture solution, by first, holding hair follicle tails with hair follicle extraction forceps, then inactivating the hair follicles with a novel vitiligo hair follicle inactivation needle under the microscope, the inactivation being performed by aligning an enlarged hair nipple and stabbing into the middle of the hair nipple until a "snap" sound is heard and the liquid runs up, so that the hair follicles are not able to enter the next hair cycle thereby putting the hair follicle in a "vegetative" state, so as to inactivate the hair follicles and realize that vitiligo only turns black without hair after surgery.

* * * * *